(12) United States Patent
Pedicini

(10) Patent No.: US 10,912,597 B2
(45) Date of Patent: Feb. 9, 2021

(54) ORTHOPEDIC ADAPTER FOR AN ELECTRIC IMPACTING TOOL

(71) Applicant: DePuy Synthes Products, Inc., Raynham, MA (US)

(72) Inventor: Christopher Pedicini, Franklin, TN (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 169 days.

(21) Appl. No.: 15/978,763

(22) Filed: May 14, 2018

(65) Prior Publication Data

US 2019/0183555 A1  Jun. 20, 2019

Related U.S. Application Data

(63) Continuation-in-part of application No. 15/939,048, filed on Mar. 28, 2018.

(Continued)

(51) Int. Cl.
*A61B 17/92* (2006.01)
*A61B 17/16* (2006.01)
(Continued)

(52) U.S. Cl.
CPC .......... *A61B 17/92* (2013.01); *A61B 17/1628* (2013.01); *B25D 11/108* (2013.01);
(Continued)

(58) Field of Classification Search
CPC . A61B 17/92; A61B 17/1626; A61B 17/1628; A61B 17/1604;
(Continued)

(56) References Cited

U.S. PATENT DOCUMENTS 2,702,550 A    2/1955  Rowe
4,922,898 A *  5/1990  Dunn ..................... A61F 2/468
                                                   606/85

(Continued)

FOREIGN PATENT DOCUMENTS

WO  WO 2017/180622 A1 * 10/2017 ............. A61B 17/16
WO      2018055501 A1    3/2018

OTHER PUBLICATIONS

U.S. Appl. No. 15/789,493 entitled "Orthopedic Impacting Device Having a Launched Mass Delivering a Controlled, Repeatable & Reversible Impacting Force" filed Oct. 20, 2017.

(Continued)

*Primary Examiner* — Andrew M Tecco
*Assistant Examiner* — Nicholas E Igbokwe

(57) ABSTRACT

An electrically driven orthopedic impactor may include an adapter for interfacing between the orthopedic impactor and a surgical implement. The adapter may have a first surface that transmits a forward impact energy and a second surface that transmits a reverse impact energy. The adapter can connect to the surgical implement and to the orthopedic impactor without the use of external tools. The adapter may connect to the orthopedic impactor via a pushing motion and may disconnect from the orthopedic impactor via a reciprocal sleeve. A sensor can communicate a spatial orientation of the adapter with respect to at least one reference point that is not located on the adapter or the orthopedic impactor. A communication device may transmit information to the orthopedic impactor related to frequency or impact energy settings based on a type of surgical implement attached to the adapter.

18 Claims, 13 Drawing Sheets

Related U.S. Application Data

(60) Provisional application No. 62/599,616, filed on Dec. 15, 2017.

(51) Int. Cl.

| | | |
|---|---|---|
| *B25D 17/00* | (2006.01) | |
| *B25D 11/10* | (2006.01) | |
| *A61B 17/00* | (2006.01) | |
| *A61B 90/30* | (2016.01) | |
| *A61B 90/00* | (2016.01) | |
| *A61B 90/98* | (2016.01) | |

(52) U.S. Cl.
CPC ........ *B25D 17/005* (2013.01); *A61B 17/1626* (2013.01); *A61B 17/1659* (2013.01); *A61B 17/1666* (2013.01); *A61B 17/1668* (2013.01); *A61B 90/98* (2016.02); *A61B 2017/00017* (2013.01); *A61B 2017/0046* (2013.01); *A61B 2017/00057* (2013.01); *A61B 2017/00115* (2013.01); *A61B 2017/00119* (2013.01); *A61B 2017/00398* (2013.01); *A61B 2017/00477* (2013.01); *A61B 2017/00734* (2013.01); *A61B 2017/924* (2013.01); *A61B 2017/927* (2013.01); *A61B 2090/0808* (2016.02); *A61B 2090/309* (2016.02)

(58) Field of Classification Search
CPC ........... A61B 2017/00477; A61B 2017/00486; A61B 2017/924; A61B 2017/927
See application file for complete search history.

(56) References Cited

U.S. PATENT DOCUMENTS

| | | | |
|---|---|---|---|
| 5,057,112 A | | 10/1991 | Sherman et al. |
| 5,169,401 A | * | 12/1992 | Lester ................ A61B 17/1659 606/79 |
| 5,352,230 A | | 10/1994 | Hood |
| 5,485,887 A | | 1/1996 | Mandanis |
| 6,344,060 B1 | * | 2/2002 | Schmotzer .......... A61F 2/30724 623/22.12 |
| 6,938,705 B2 | | 9/2005 | Kikuchi |
| 8,393,409 B2 | | 3/2013 | Pedicini |
| 8,602,124 B2 | | 12/2013 | Pedicini |
| 8,695,726 B2 | | 4/2014 | Pedicini |
| 8,936,105 B2 | | 1/2015 | Pedicini |
| 8,936,106 B2 | | 1/2015 | Pedicini |
| 9,901,354 B2 | | 2/2018 | Pedicini |
| RE46,954 E | | 7/2018 | Pedicini |
| RE46,979 E | | 8/2018 | Pedicini |
| 2005/0065529 A1 | | 3/2005 | Liu et al. |
| 2006/0278680 A1 | | 12/2006 | Viola et al. |
| 2011/0064978 A1 | | 3/2011 | McGahan et al. |
| 2012/0029354 A1 | * | 2/2012 | Mark ................ A61B 17/32002 600/439 |
| 2012/0232556 A1 | | 9/2012 | Mani et al. |
| 2013/0161050 A1 | * | 6/2013 | Pedicini ................. B25D 17/00 173/201 |
| 2014/0100687 A1 | | 4/2014 | Ekstrom et al. |
| 2015/0005777 A1 | | 1/2015 | Ferro et al. |
| 2015/0150547 A1 | * | 6/2015 | Ingmanson ...... A61B 17/07207 606/1 |
| 2015/0182233 A1 | | 7/2015 | Van Wyk et al. |
| 2015/0196343 A1 | | 7/2015 | Donald et al. |
| 2016/0095613 A1 | * | 4/2016 | Trondle .......... A61B 17/32002 606/171 |
| 2016/0199199 A1 | | 7/2016 | Pedicini |
| 2016/0218404 A1 | | 7/2016 | Pedicini |
| 2017/0020536 A1 | | 1/2017 | Johnson et al. |
| 2017/0367714 A1 | | 12/2017 | McCulloch et al. |
| 2018/0013184 A1 | | 1/2018 | Pedicini |
| 2018/0055518 A1 | | 3/2018 | Pedicini |
| 2018/0055552 A1 | | 3/2018 | Pedicini |
| 2018/0055553 A1 | | 3/2018 | Pedicini |
| 2018/0055554 A1 | | 3/2018 | Pedicini |
| 2018/0116681 A1 | | 5/2018 | Pedicini |
| 2018/0325527 A1 | | 11/2018 | Wozencroft |
| 2019/0183554 A1 | | 6/2019 | Pedicini |

OTHER PUBLICATIONS

U.S. Appl. No. 15/939,048, filed May 14, 2018, Christopher Pedicini, Orthopedic Adapter for an Electric Impacting Tool.
International Search Report and Written Opinion for PCT/US18/24934 dated Aug. 3, 2018 (13 pages).
Extended European Search Report issued in European Application No. 19173613.1, dated Oct. 18, 2019, 9 pages.

* cited by examiner

ORTHOPEDIC ADAPTER FOR AN ELECTRIC IMPACTING TOOL

RELATED APPLICATIONS

This application claims priority to U.S. Provisional Patent Application Ser. No. 62/599,616, entitled "Orthopedic Adapter for an Electric Impacting Tool," filed Dec. 15, 2017; and is a continuation-in-part of U.S. patent application Ser. No. 15/939,048, entitled "Orthopedic Adapter for an Electric Impacting Tool," filed Mar. 28, 2018. This application is related to the following prior patent applications directed to Orthopedic Impacting Devices: U.S. patent application Ser. No. 12/980,329, entitled "Electric Motor Driven Tool for Orthopedic Impacting," filed Dec. 29, 2010, now U.S. Pat. No. 8,695,726; U.S. patent application Ser. No. 13/466,870, entitled "Electric Motor Driven Tool for Orthopedic Impacting," filed May 8, 2012, now U.S. Pat. No. 8,393,409; U.S. patent application Ser. No. 13/790,870, entitled "Electric Motor Driven Tool for Orthopedic Impacting," filed Mar. 8, 2013, now U.S. Pat. No. 8,602,124; U.S. patent application Ser. No. 14/250,102, entitled "Electric Motor Driven Tool for Orthopedic Impacting," filed Apr. 10, 2014, now U.S. Pat. No. 9,901,354; U.S. patent application Ser. No. 14/332,767, entitled "Electric Motor Driven Tool for Orthopedic Impacting," filed Jul. 16, 2014, now U.S. Pat. No. 8,936,105; U.S. patent application Ser. No. 14/332,790, entitled "Electric Motor Driven Tool for Orthopedic Impacting," filed Jul. 16, 2014, now U.S. Pat. No. 8,936,106; U.S. patent application Ser. No. 14/850,588, entitled "Electric Motor Driven Tool for Orthopedic Impacting," filed Sep. 10, 2015; U.S. patent application Ser. No. 14/850,620, entitled "Electric Motor Driven Tool for Orthopedic impacting," filed Sep. 10, 2015; U.S. patent application Ser. No. 14/850,639, entitled "Electric Motor Driven Tool for Orthopedic Impacting," filed Sep. 10, 2015; U.S. patent application Ser. No. 14/850,660, entitled "Electric Motor Driven Tool for Orthopedic Impacting," filed Sep. 10, 2015; U.S. patent application Ser. No. 14/850,674, entitled "Electric Motor Driven Tool for Orthopedic impacting," filed Sep. 10, 2015; U.S. patent application Ser. No. 14/850,695, entitled "Electric Motor Driven Tool for Orthopedic Impacting," filed Sep. 10, 2015; U.S. patent application Ser. No. 14/992,781, entitled "Electric Motor Driven Tool for Orthopedic Impacting," filed Jan. 11, 2016; U.S. patent application Ser. No. 15/009,723, entitled "Battery Enclosure for Sterilizeable Surgical Tools Having Thermal Insulation," filed Jan. 28, 2016; U.S. patent application Ser. No. 15/098,662, entitled "Electric Motor Driven Tool for Orthopedic Impacting," filed Apr. 14, 2016; U.S. patent application Ser. No. 15/439,692; entitled "Orthopedic Impacting Device Having a Launched Mass Delivering a Controlled, Repeatable & Reversible Impacting Force," filed Feb. 22, 2017; U.S. patent application Ser. No. 15/446,862, entitled "Orthopedic Impacting Delivering a Controlled, Repeatable Impact," filed Mar. 1, 2017; U.S. patent application Ser. No. 15/544,317, entitled "Battery Enclosure for Sterilizeable Surgical Tools Having Thermal Insulation," filed Jul. 18, 2017; U.S. patent application Ser. No. 15/600,234, entitled "Orthopedic Impacting Delivering a Controlled, Repeatable Impact," filed May 19, 2017; U.S. patent application Ser. No. 15/600,284, entitled "Orthopedic Impacting Device Having a Launched Mass Delivering a Controlled, Repeatable & Reversible Impacting Force," filed May 19, 2017; U.S. patent application Ser. No. 15/677,933, entitled "Electric Motor Driven Tool for Orthopedic Impacting," filed Aug. 15, 2017; U.S. patent application Ser. No. 15/789,493, entitled "Orthopedic Impacting Device Having a Launched Mass Delivering a Controlled, Repeatable &. Reversible Impacting Force," filed Oct. 20, 2017; and U.S. patent application Ser. No. 15/857,385, entitled "Electric Motor Driven Tool for Orthopedic Impacting," filed. Dec. 28, 2017. All above identified applications are hereby incorporated by reference in their entireties.

BACKGROUND

The present disclosure relates to adapters for electrically powered surgical impacting tools used in surgical applications such as orthopedic procedures, including procedures using a motor driven tool for bidirectional, surgical impacting that is driven by a launched mass to provide controlled, repeatable impacts to a surgical implement.

In the field of orthopedics, prosthetic devices, such as artificial joints, are often implanted or seated in a patient's bone cavity. The cavity is typically formed during surgery before a prosthesis is seated or implanted. For example, a physician may remove and or compact existing bone to form the cavity. The prosthesis usually includes a stem or other protrusion that is inserted into the cavity.

To create the cavity, a physician may use a broach conforming to the shape of the stem of the prosthesis. Solutions known in the art include providing a handle with the broach for manual hammering by the physician during surgery to impel the broach into the implant area. Unfortunately, this approach is crude and notoriously imprecise, leading to unnecessary mechanical stress on the bone. The results can be unpredictable and depend on the skill of a particular physician. Historically, this approach will in many cases result in inaccuracies in the location and configuration of the cavity. Additionally, the surgeon is required to expend an unusual amount of physical force and energy to hammer the broach and to manipulate the bones and prosthesis. Most importantly, this approach carries with it the risk that the physician will cause unnecessary further trauma to the surgical area and damage otherwise healthy tissue, bone structure and the like.

Another technique for creating the prosthetic cavity is to drive the broach pneumatically, that is, by compressed air. This approach is disadvantageous in that it prevents portability of an impacting tool, for instance, because of the presence of a tethering air line air being exhausted from a tool into the sterile operating field and fatigue of the physician operating the tool. This approach, as exemplified in U.S. Pat. No. 5,057,112, does not allow for precise control of the impact force or frequency and instead fractions very much like a jackhammer when actuated. Again, this lack of any measure of precise control makes accurate broaching of the cavity more difficult and can lead to unnecessary patient complications and trauma. These types of tools may produce movements with wide ranges of motion perpendicular to the cutting axis, further inhibiting accuracy and precision. In some instances, such accuracy and precision, or lack thereof, may be quantified by describing the total indicator reading ("TIR") of the surgical implement connected to the tool's adapter. The TIR, for example, is a measurement describing the deviation in contour along a surface (e.g., planar, cylindrical, etc.). In a particular example, the TIR of the adapter may represent the adapter's "flatness" along an example surface.

A third technique relies on computer-controlled robotic arms for creating the cavity. While this approach overcomes the fatiguing and accuracy issues, it suffers from having a very high capital cost and removes the tactile feedback that a surgeon can get from a manual approach. Further unless the approach is by milling, an impacting means (pneumatic, electrical or manual) is still required.

Other techniques use the inventor's own work and may include a hammer throwing method which involves a linear compressor, vacuum actuation, or a mechanical or gas spring, all of which are electrically powered. With the hammer throwing method, however, the use of existing commercially available adapters to couple impact energy created by the thrown mass (hammer) or striker from within the electrically driven impactor to a surgical implement has resulted in very poor coupling of the internal energy to the surgical implement, with losses of 50% or greater being typical.

Consequently, there exists a need for improved adapters between impacting tools and surgical implements that overcome the various disadvantages of existing adapters.

SUMMARY OF ILLUSTRATIVE EMBODIMENTS

In view of the foregoing disadvantages, adapters are provided for an electric motor-driven orthopedic impacting tool to enable coupling of surgical implements to the tool, which may be provided for orthopedic impacting in hips, knees, shoulders and the like. The adapter is capable of holding a broach, chisel, or other end effector and delivering power from the impactor to gently tap the broach, chisel or other end effector into the cavity with controlled percussive impacts, resulting in a better fit for the prosthesis or the implant. The adapter can also be used in the placement and removal of broaches, implants, cups, liners, head balls, nails, wires, pins, and other devices. Further, the adapter may enable additional control of the electrically driven orthopedic impactor by communicating or otherwise indicating impact settings based on the patient, surgical implement, or surgical procedure. The adapter further enables proper seating and, in the case of bidirectional movement, the removal of the prosthesis or the implant into or out of an implant cavity, and advantageously augments the existing surgeon's skill in guiding the electrically driven orthopedic impactor.

In order to provide context, a brief description of the electrically driven orthopedic impactor is provided (other similar and related devices are also described in the Related Applications identified above and incorporated by reference herein). An electric motor-driven orthopedic impacting tool includes a power source (such as a battery, fuel cell, or cartridge of compressed gas), a motor assembly, a controller, a housing, a stored-energy system or mechanism such as a gas or mechanical spring capable of storing and releasing potential energy, and a striker energized by the stored-energy drive system to be operational in a forward and/or a rearward direction, where the striker is capable of generating an impact force in either a forward or a rearward direction.

In an embodiment, an adapter is used to communicate the force between the electrically driven impactor and the surgical implement. In a further embodiment, the adapter has two distinct surfaces which are used to communicate a forward or reverse impact from the electrically driven impactor (hereafter referred to as tool) to the surgical implement.

In an embodiment the surgical implement can be combined with the adapter.

In an embodiment, the adapter communicates at least 50% of the energy of the striker to the surgical implement.

In an exemplary embodiment, the adapter communicates back to the tool whether the surgeon or robot is either pushing or pulling the adapter and surgical implement towards or away from the patient.

In a further exemplary embodiment, a surgical implement (e.g., broach, chisel or other end effector) can be rotated to a number of positions while still maintaining axial alignment, as illustrated, for example, in FIG. 2A, where the adapter is rotatable in four different positions, each position rotated by 90°. This facilitates the use of the adapter or broach, for example, in various anatomical presentations during surgery.

In some embodiments, the adapter is configured to communicate the spatial position of the adapter in relation to the patient. For example, the adapter or the impactor may include a sensor and/or a camera that communicates the relative position and/or alignment of the tool to the patient. This may be accomplished by tracking a reference point associated with the patient and not located on the adapter or the impactor. In a further embodiment, the sensor may be configured to communicate the position of the adapter or impactor in coordination with a surgical navigation system to inform a surgeon or robot of a position in comparison to an optimal position, a planned final position, or any other desired position.

In an exemplary embodiment, the adapter of the tool includes at least one of two points of impact, a forward striking surface or first surface and a rearward striking surface or second surface.

In an exemplary embodiment, the anvil and the adapter include a single element, or one may be integral to the other.

In an exemplary embodiment, the adapter weighs less than the anvil, striker, or other thrown mass of the impactor.

In an exemplary embodiment, the adapter weighs less than half of the weight of the impactor tool, and preferably less than 40% of the weight of the impactor.

In an exemplary embodiment, the adapter is substantially axially inline with the anvil, striker, or other thrown mass of the impactor. This has an unexpected benefit in that bone is an anisotropic material, which is strongest with respect to compression forces, then tension, then shear. By keeping the forces inline, operation of the tool will result in lower stress on the bone and yield better outcomes.

In an exemplary embodiment, the adapter is able to communicate force, frequency, and throw settings back to the tool based on the surgical implement or procedure.

In an exemplary embodiment, the adapter may include a dampening mechanism such as a viscoelastic material or elastomeric or mechanical spring which limits the total energy communicated from the tool to the surgical implement. The dampener may be chosen or configured to provide any desired capability, such as a particular level of dampening or dampening only in a particular direction. For example, the dampener may reduce the impact energy from the tool by 10% or 50%, preferably at least 20%, and the dampener may only dampen energy in the forward direction, leaving a sharper impact force in the rearward direction.

In an exemplary embodiment, the adapter may include a mechanism that produces an audible or visual cue that indicates that the adapter is properly connected to the tool. For example, tabs, grooves, raised edges, and other similar features may be configured to snap into place and generate an audible cue upon proper connection of the adapter to the tool or surgical implement. A visual cue may also show that the adapter is properly connected to the tool or surgical implement. For example, a window or other designated area on the adapter, tool, or surgical implement may display a red color when the adapter is not properly connected and a green color when the adapter is properly connected.

In an exemplary embodiment, the adapter may be connected to a surgical implement having cutting teeth useful for final shaping of bone prior to placing an implant. In a still further embodiment, the pitch of the cutting teeth (spacing in the direction of impact) is determined to be less than the powered throw of the instrument. In a still further embodiment, it was found to be advantageous to have bidirectional cutting teeth, which allowed for bone shaping on both a forward impact and a rearward impact.

These, together with other aspects of the present disclosure, along with the various features of novelty that characterize the present disclosure, are pointed out with particularity in the claims annexed hereto and form a part of the present disclosure. For a better understanding of the present disclosure, its operating advantages, and the specific non-limiting objects attained by its uses, reference should be made to the accompanying drawings and detailed description in which there are illustrated and described exemplary embodiments of the present disclosure.

The forgoing general description of the illustrative implementations and the following detailed description thereof are merely exemplary aspects of the teachings of this disclosure, and are not restrictive.

BRIEF DESCRIPTION OF THE DRAWINGS

The accompanying drawings, which are incorporated in and constitute a part of the specification, illustrate one or more embodiments and, together with the description, explain these embodiments. The accompanying drawings have not necessarily been drawn to scale. Any values dimensions illustrated in the accompanying graphs and figures are for illustration purposes only and may or may not represent actual or preferred values or dimensions. Where applicable, some or all features may not be illustrated to assist in the description of underlying features. In the drawings.

DETAILED DESCRIPTION OF ILLUSTRATIVE EMBODIMENTS

Figure 1:
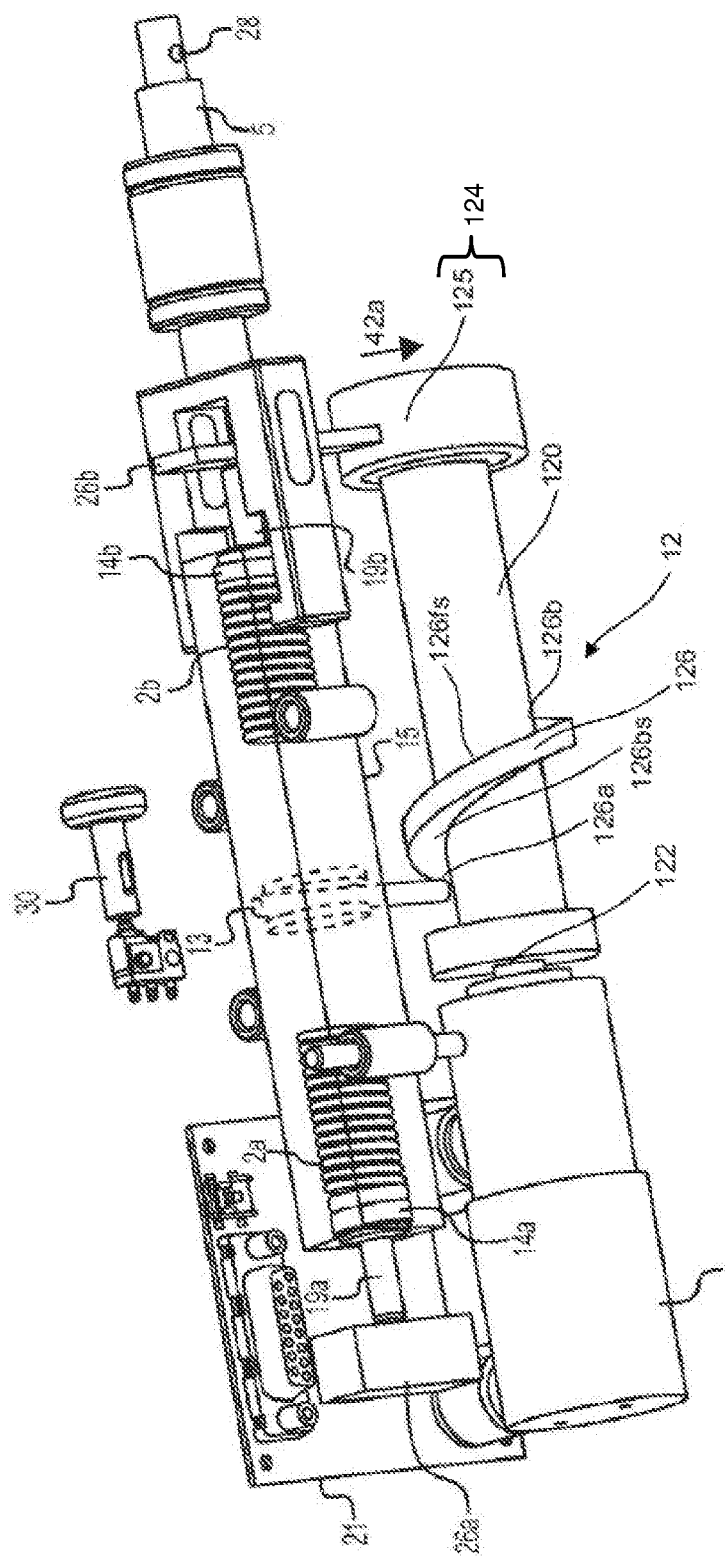
FIG. 1 illustrates a perspective view of an orthopedic impacting tool according to an embodiment.

The description set forth below in connection with the appended drawings is intended to be a description of various, illustrative embodiments of the disclosed subject matter. Specific features and functionalities are described in connection with each illustrative embodiment; however, it will be apparent to those skilled in the art that the disclosed embodiments may be practiced without each of those specific features and functionalities.

Reference throughout the specification to "one embodiment" or "an embodiment" means that a particular feature, structure, or characteristic described in connection with an embodiment is included in at least one embodiment of the subject matter disclosed. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments. Further, it is intended that embodiments of the disclosed subject matter cover modifications and variations thereof.

It must be noted that, as used in the specification and the appended claims, the singular forms "a," "an," and "the" include plural referents unless the context expressly dictates otherwise. That is, unless expressly specified otherwise, as used herein the words "a," "an," "the," and the like carry the meaning of "one or more." Additionally, it is to be understood that terms such as "left," "right," "top," "bottom," "front," "rear," "side," "height," "length," "width," "upper," "lower," "interior," "exterior," "inner," "outer," and the like that may be used herein merely describe points of reference and do not necessarily limit embodiments of the present disclosure to any particular orientation or configuration. Furthermore, terms such as "first," "second," "third," etc., merely identify one of a number of portions, components, steps, operations, functions, and/or points of reference as disclosed herein, and likewise do not necessarily limit embodiments of the present disclosure to any particular configuration or orientation.

Furthermore, the terms "approximately," "about," "proximate," "minor variation," and similar terms generally refer to ranges that include the identified value within a margin of 20%, 10% or preferably 5% in certain embodiments, and any values therebetween.

All of the functionalities described in connection with one embodiment are intended to be applicable to the additional embodiments described below except where expressly stated or where the feature or function is incompatible with the additional embodiments. For example, where a given feature or function is expressly described in connection with one embodiment but not expressly mentioned in connection with an alternative embodiment, it should be understood that the inventor intends that that feature or function may be deployed, utilized or implemented in connection with the alternative embodiment unless the feature or function is incompatible with the alternative embodiment.

Describing now an exemplary tool with which the improved adapter may communicate, a motor-driven orthopedic impacting tool is provided with controlled percussive impacts. The motor may be electric, such as a brushless, autoclavable motor such as those generally available from Maxon Motor® and/or Portescap®. The motor may be battery-operated. The energy supply to the orthopedic impacting tool may provide wireless portability and communication for the orthopedic impacting tool. The tool may include the capabilities to perform single and multiple impacts, as well as impacting of variable and varying directions, forces, and frequencies. In some embodiments, the impact energy is adjustable. In certain embodiments, the impact is transferred to a surgical implement such as a broach, chisel, or other end effector connected to the tool.

In some embodiments, the tool includes a housing. The housing may securely cover and hold at least one component of the tool and may be formed of a material suitable for surgical applications, such as aluminum or Polyphenylsulfone (PPSF or PPSU), also known as Radel®. In some embodiments, the housing contains a motor assembly, at least one reducing gear, a spring element, a striker or launched mass, a control circuit or module, an anvil, a first or forward striking surface for forward impact, and a different, second or rearward striking surface for rearward impact. The motor assembly may include a linear motion converter to convert a rotary motor drive. The spring element may be a mechanical, elastomeric, or gas spring.

The tool further may include a handle portion with an optional hand grip for comfortable and secure holding of the tool, or a suitable mount interface for integrating the tool into a robotic assembly while in use, and an adapter, a battery, a positional sensor, a directional sensor, and a torsional sensor. The tool may further deliver focused illumination by way of a semiconductor light source, such as an LED or traditional incandescent light source, to provide light in the surgical work area in which a surgeon employs the tool. The anvil may be coupled to a surgical implement broach, chisel or other end effector known in the art through the use of an interfacing adapter, which adapter may have a quick connect mechanism to facilitate rapid change of different broaching sizes. The tool may further include an axially locking, but rotationally variable, feature to allow the adapter to be positioned in different spatial fashions as to gain tissue clearance for tool features such as the handle.

In some embodiments, an axis of the launched or thrown mass is aligned axially, along the direction of movement, to within 20 degrees of the axis of the adapter, and more preferably, to within 10 degrees of the axis of the adapter. Such axial alignment is significant in terms of maximizing the energy transferred to the surgical implement, as well as minimizing the generation of off-axis forces, which can contribute to adverse surgical outcomes, such as fractures. The inventor discovered that these benefits of axial alignment were, in part, a result of bone being an anisotropic material, rendering it stronger with respect to compression or tension forces than it is with respect to shear forces.

Figure 4:
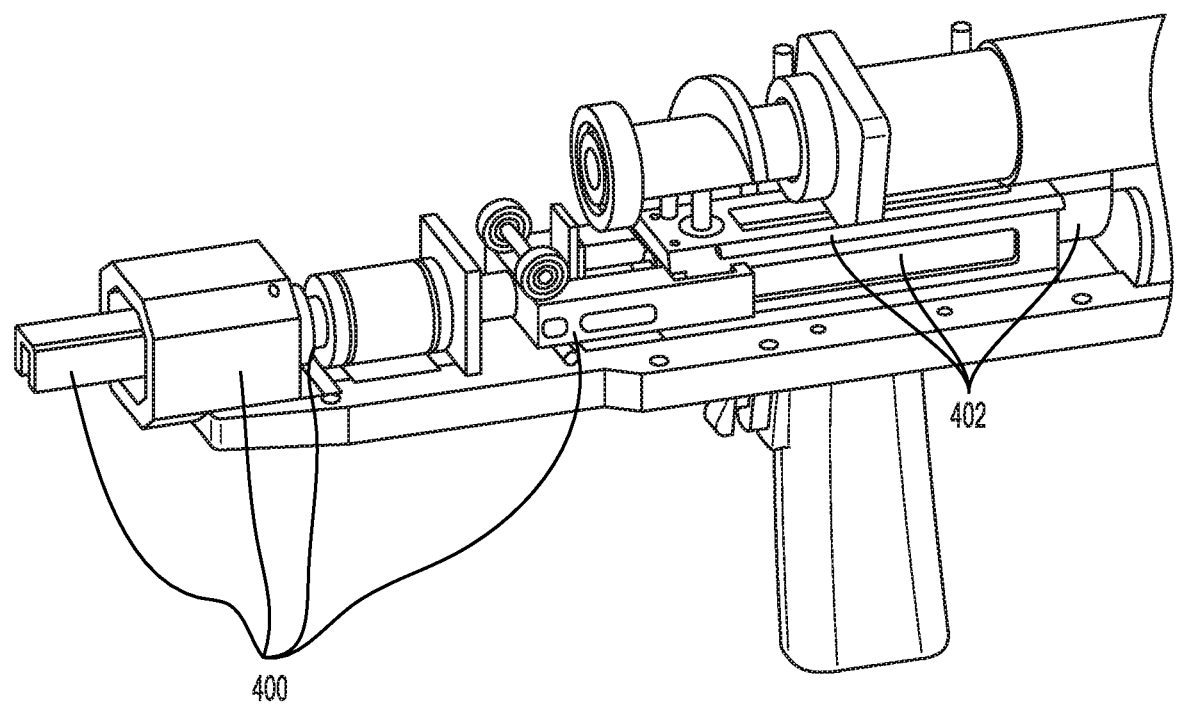
FIG. 4 shows exemplary masses of an impacting tool for calculating mass ratios.

It has been determined by the inventor that the mass ratios and materials used for the launched or thrown mass, the anvil, and the adapter are significant in terms of how effectively the kinetic energy of the thrown mass is conveyed to the surgical implement. For purposes of certain embodiments, the ratio of the delivered energy to the surgical implement as a function of the kinetic energy in the thrown mass or striker is referred to as the transfer function. The transfer function is used as a measure of performance, in terms of how efficiently the tool is performing broaching, impacting, or extraction surgical procedures. For example, in one design in which the thrown mass, anvil, and adapter were all made of hardened stainless steel, the ratio of the energy conveyed to the surgical implement to the kinetic energy of the thrown mass, or the transfer function, was found to be less than 50%. By increasing the mass ratio of the thrown mass to the impacted mass (the sum of the mass of the anvil, the adapter, and the surgical implement), the efficiency of the adapter and the system, in particular, the transfer function of the adapter and the system, was increased to greater than 60%, and in many cases, close to 75%. FIG. 4 shows an embodiment of the tool and illustrates the aforementioned masses, including impacted mass 400 and thrown mass 402.

The tool, in further embodiments, includes a compliance element inserted between the striker and the adapter. Preferably, the compliance element is a resilient material that recovers well from impact and imparts minimal damping on the total energy. As an example, a urethane component could be inserted at the interface where the striker impacts the anvil. In another example, the compliance element may be inserted in such a fashion that it only reduces the impact force in the forward direction and does not affect the desire for a sharp impact force in the rearward direction. This type of compliance element can limit the peak force during impact to preclude such peaks from causing fractures in the patient's bone, yet maintain the high peak force necessary to be able to retract stuck broaches or other surgical implements.

In some embodiments, the impactor is coupled to a robot, for example, thus potentially eliminating the need for a portable power source (battery) and/or hand grip on the tool.

In some embodiments, the coupling of the adapter to the tool includes a linkage arrangement or other adjustment mechanisms known in the art such that the position of the surgical implement (broach, chisel or other end effector) can be modified without requiring the surgeon to rotate the tool.

FIG. 1 shows a perspective view of an example of an orthopedic impacting tool with which an improved adapter may communicate. A motor 8 of a mechanical spring assembly system, in combination with a linear motion converter, which includes a barrel or cylindrical cam 12 and a cam follower 13, actuates a first spring piston 19a and/or a launched mass or striker 15, in order to ultimately generate a forward impact force is provided (also provided is a second spring piston 19b to engage a second spring 2b being compressed against a second pusher plate 26b to generate a rearward impact force). It is to be noted that the piston generally refers to a thrusting or push off element and can have any of a number of shapes. The spring assembly system further includes, in some embodiments, an anvil 5.

The barrel cam 12 can include a cylindrical portion 120 mounted longitudinally on a shaft 122 extending between the motor 8 and a bearing support 124, and a worm 126 protruding radially from the cylindrical portion 120 and helicoidally along a length of the cylindrical portion 120 from a first worm end 126a to a second worm end 126b.

The bearing support 124 can include a housing 125 supported by the second pusher plate 26b and a bearing nested in the housing 125 to support the shaft 122.

The worm 126 can include a backward surface 126bs, e.g. the surface facing a first pusher plate 26a, and a forward surface 126fs of the worm 126, e.g. the surface facing the second pusher plate 26b, that contacts the cam follower 13 and forces the cam follower 13 to follow a rectilinear movement between the first worm end 126a and the second worm end 126b as the worm 126 rotates.

The cam follower 13 can be displaced along the worm 126 in the forward direction, e.g. towards the second pusher plate 26b, by having the cam follower 13 contacting the forward surface 126fs of the worm 126 and having the worm 126 rotating in a first direction 42a.

Figure 1A:
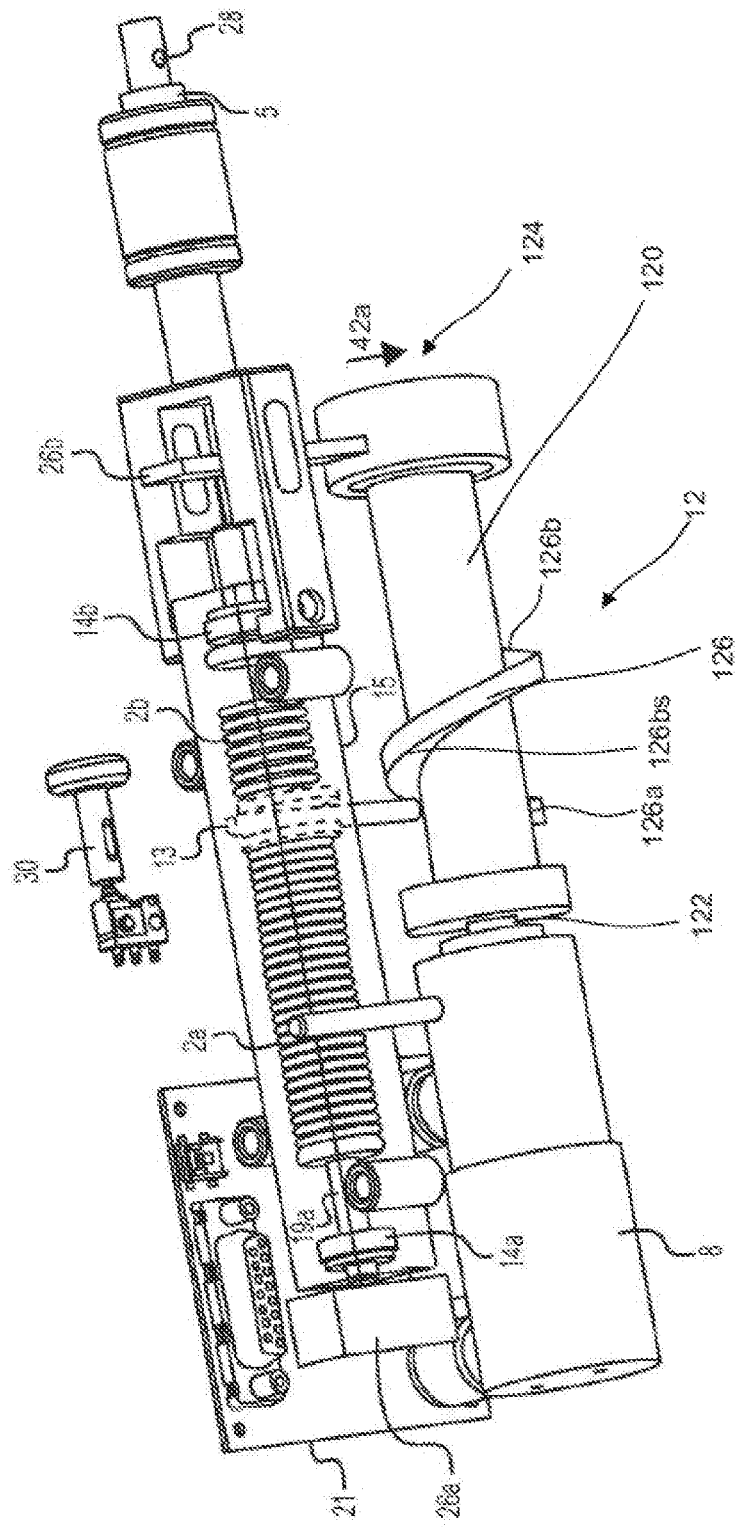
FIG. 1A illustrates a perspective view of the tool in FIG. 1 in which the barrel or cylindrical cam positions the piston in the operative position for release for a forward impact.
Figure 1B:
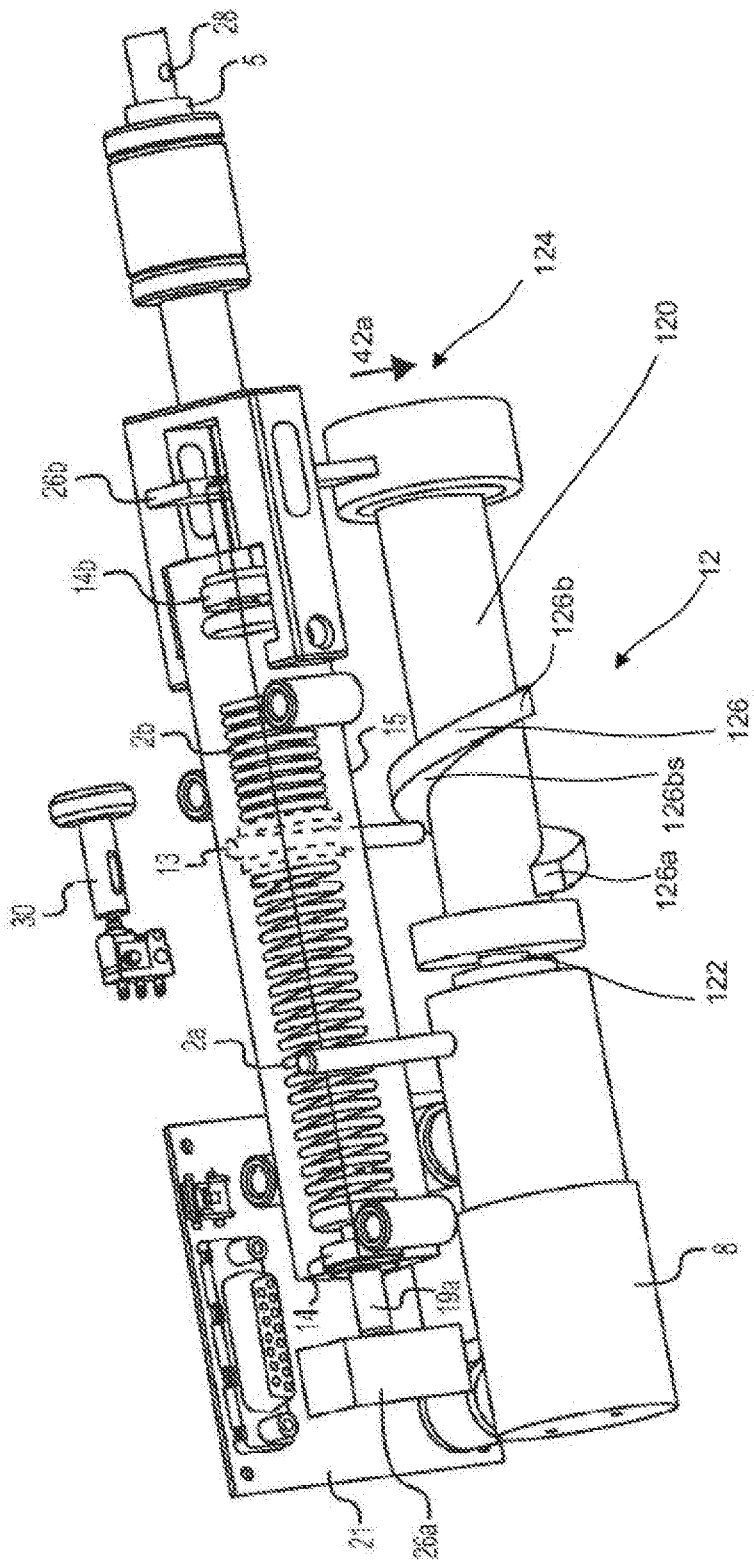
FIG. 1B illustrates a perspective view of the tool in FIG. 1 in which after the Stored-energy has been released, a launched mass is accelerated towards a point of impact in a forward direction.

The cam follower 13 can be displaced along the worm 126 in the backward direction, e.g. towards the first pusher plate 26a, by having the cam follower 13 contacting a backward surface 126bs of the worm 126, e.g. the surface facing the pusher plate 26a, and having the worm 126 rotating in a second direction opposite to the first direction 42a, as illustrated in FIGS. 1, 1A, and 1B.

Bumpers 14a and 14b function as stoppers to prevent end faces of the piston 19a and 19b from impacting the striker 15.

The barrel cam 12 can enhance efficiency of the orthopedic impacting tool by allowing the motor 8 to rotate with larger angles compared to a conventional linear motion converter that may rely on conventional vertical cams that hit the cam follower 13 through small repetitive strokes. That is, the barrel cam 12 allows the use of more radians of rotation for the motor to get the energy and thus, reduces the current drain on the battery significantly. Accordingly, a single primary battery could be used in certain embodiments by utilizing the advantages provided by the barrel cam 12 in the reduction of the current drain.

In addition, the barrel cam 12 can in certain cases allow for the elimination of an intermediate gear assembly, as the barrel cam 12 can be directly mounted onto the shaft 122 and thus enhance efficiency whilst reducing the cost of the orthopedic tool.

The first piston 19a engages a first spring 2a, which can for example be either a mechanical or gas spring. In the mechanical spring assembly system, the deflection in relation to a free length of the spring is preferably less than 50%. Music wire or, more preferably, stainless steel or titanium are suitable materials for the spring. Preferably, the spring is a compression spring, although other types of springs are contemplated. An internal spring guide may also be included, for example with metal compression springs, to substantially quiet the tool in operation, thereby improving the noise profile and hence the user ergonomics. In the gas spring assembly system, the gas spring operates under pressure in a range of about 100 to 3000 psi, for example. The gas spring is preferably initially charged with a non-oxidizing gas, such as nitrogen, or an inert gas, such as argon. Advantageously, nitrogen has a lower permeation rate through seals of the gas spring, resulting in a potentially longer shelf life for the seals and the spring itself.

FIG. 1A further illustrates the example tool of FIG. 1 in which the barrel cam 12 used for actuating the first piston 19a has the first piston 19a "cocked" in the operation position ready for release, or stated another way, the motor 8 rotates the shaft 122 which rotates the barrel cam 12, the first worm end 126a of the worm 126 contacts the can follower 13 and the cam follower 13 linearly slides along the backward surface 126bs and compresses the first piston 19a against the first pusher plate 26a, thus storing potential energy within the first spring 2a. In the "cocking phase" the first piston 19a, in combination with the launched mass or striker 15, contacts and is pushed by the cam follower 13, which is driven by the worm 126 of the barrel cam 12 that rotates under the action of the motor 8. As the barrel cam 12 and worm 126 continue to rotate, energy stored inside the first spring 2a increases until the first worm end 126a moves past the cam follower 13 to let the cam follower 13 jump from the first worm end 126a to the second worm end 126b. The striker (or launched mass) 15 is now free to travel under the stored potential energy of the first spring 2a. In particular, after a sufficient displacement of the first piston 19a, and after the barrel cam 12 releases the first piston 19a and/or the launched mass 15, the first piston 19a moves in the forward direction, and, at the same time, accelerates the launched mass or striker 15, which is in contact with the face of the first 19a. As shown, for example, in FIG. 1B, the first piston 19a releases from the striker 15, launching it towards the anvil 5.

The tool, in some embodiments, facilitates controlled continuous impacting, which impacting is dependent on a position of the trigger switch 30 operatively coupled to the power source or motor, for example. For such continuous impacting, after the trigger switch is activated, and depending on the position of the trigger switch 30, the tool may go through complete cycles at a rate proportional to the position of the trigger switch, for example. Thus, in either the single impact or continuous impacting operational modes, the creation or shaping of the surgical area may be easily controlled by the surgeon.

In some embodiments, the controlled continuous impacting is managed at least in part by a controller 21. The controller 21, for example, may include processing circuitry for monitoring and managing timing of the continuous impacting mode. In some examples, the controller 21 may include a microcontroller, system on a chip, programmable logic device, and/or microprocessor including timing circuitry for timing energy release of the surgical impacting tool. The controller may be in communication with a power source, such as a battery housed upon or within the surgical impacting device or a power connector to a separate power source.

The controller 21, in certain embodiments, includes instructions stored to a non-transitory computer readable medium which, when executed, cause the controller 21 to manage energy storage and release to enable the repeatable continuous impacting. The controller 21, in some implementations, includes one or more receivers for receiving signals from one or more communication devices or sensors, such as a positional sensor, an RFID tag, a proximity sensor, or a motion sensor. The instructions, for example, may include instructions configured to start impacting, pause impacting, and/or adapt timing of energy storage and release based upon signals received from one or more sensors or other communication devices.

The controller, in some implementations, includes one or more output elements for issuing signals to other elements of the surgical impacting device. In some embodiments, the controller includes an audio output device to issue an audible alert to an operator based upon an event, such as a low power event or a suspected mechanical failure event.

In some embodiments, as the barrel cam 12 assembly completes its course, e.g. the cam follower 13 is displaced along either the backward surface 126bs or the forward surface 126fs between the first worm end 126a and the second worm end 126b, it preferably activates the sensor 28 coupled operatively to the controller 21. The sensor 28 assists in the regulation of the preferred cyclic operation of the barrel cam 12. For example, the sensor 28 may signal the motor 8 to stop such that the barrel cam 12 is at or near a point of minimal potential energy storage. Thus, in one complete cycle, a forward or a rearward impacting force may be applied on the broach, chisel, or other end effector, or on the implant or prosthesis. In a further embodiment, it may be advantageous to insert a delay or count the number of impacts for any give procedure before starting the next cycle, making it possible to accurately control the speed of impacting, and, in turn, allowing the surgeon to accurately control the rate of energy delivery in any given operation. In a still further embodiment, it may be advantageous to stop the barrel cam 12 near a point of maximum potential energy storage to reduce a latency in the surgeons' hands. Latency, as defined, is the time between when the surgeon (or user) activates the orthopedic impacting tool and the tool actually delivers an impact. It has been determined by the inventor that latencies of around 100 milliseconds or less appear essentially as an instantaneous response. By stopping the barrel cam 12 at a point where at least part of the potential energy has been stored, the tool has the effect of near instantaneous release of the potential energy upon actuation of a tool trigger 30.

Referring now generally to FIGS. 2A-8, an orthopedic impactor is shown with various configurations of adapters for use therewith.

Figure 2A:
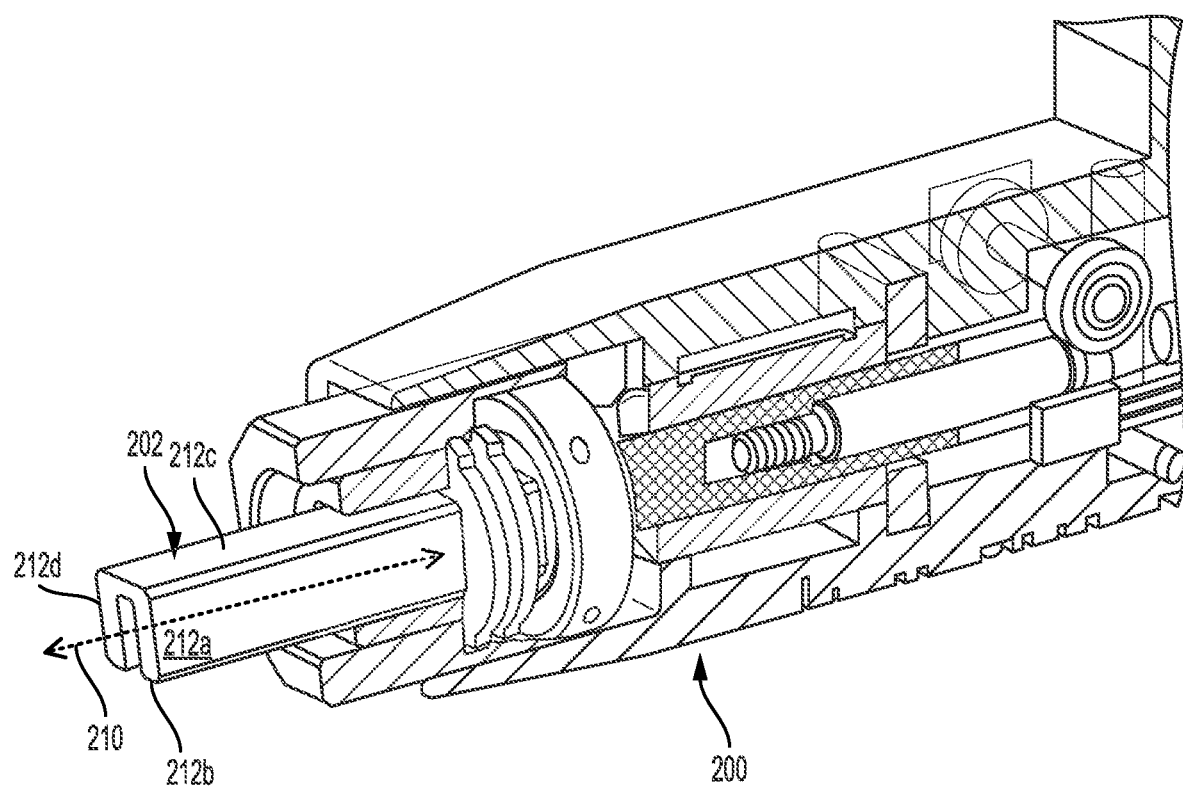
FIG. 2A shows a view of an example adapter with an impactor which has 4 different degrees of rotation around the impaction axis according to an embodiment.

FIG. 2A illustrates a surgical impactor 200 and adapter 202 in which the adapter 202 can be inserted into the impactor 200 in any of 4 different rotations around an impacting axis 210. For example, as illustrated in FIG. 2A, an impacting axis 210, or the axis along which an anvil or a mass is thrown, is oriented horizontally lengthwise leftward and rightward as drawn, and the adapter 202 has a generally square cross-section with at least four surfaces 212a, 212b, 212c, 212d that form at least four distinct planes around the lengthwise axis of the adapter 202. Those planes run parallel with the impacting or anvil axis and permit the adapter 202 to be inserted into the impactor 200 in the 4 different rotational orientations. Of course, while insertion via 4 different rotations are shown via the illustrated square interface in FIG. 2A, additional rotational positions would be possible. For example, an adapter with a hexagonal interface could have 6 different rotational configurations, and an adapter with an octagonal interface could have 8 different rotational configurations. The different insertion angles allow for multiple positioning of the surgical implement while maintaining the ability of the surgeon to hold the tool in a more ergonomic orientation.

Figure 2B:
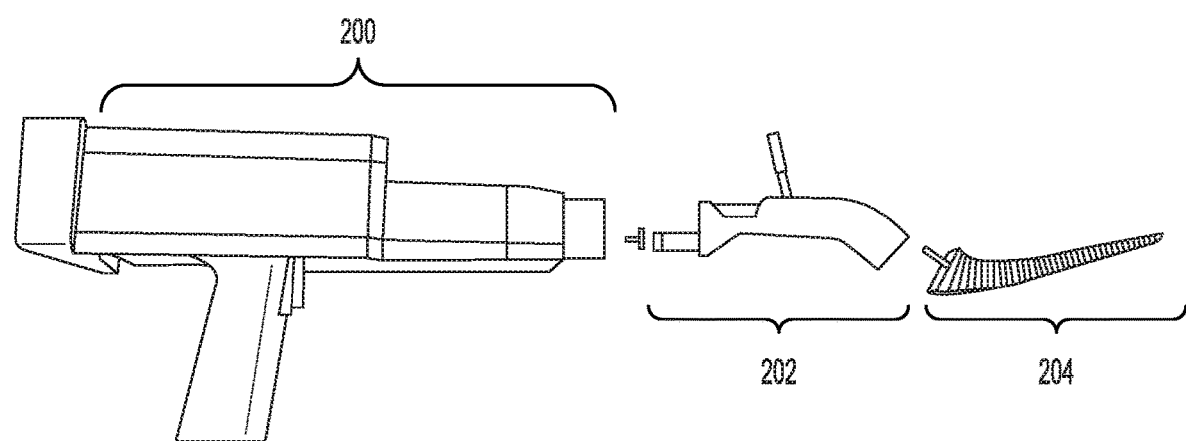
FIG. 2B shows an example impactor, adapter, and surgical implement as three separate pieces according to an embodiment.
Figure 2C:
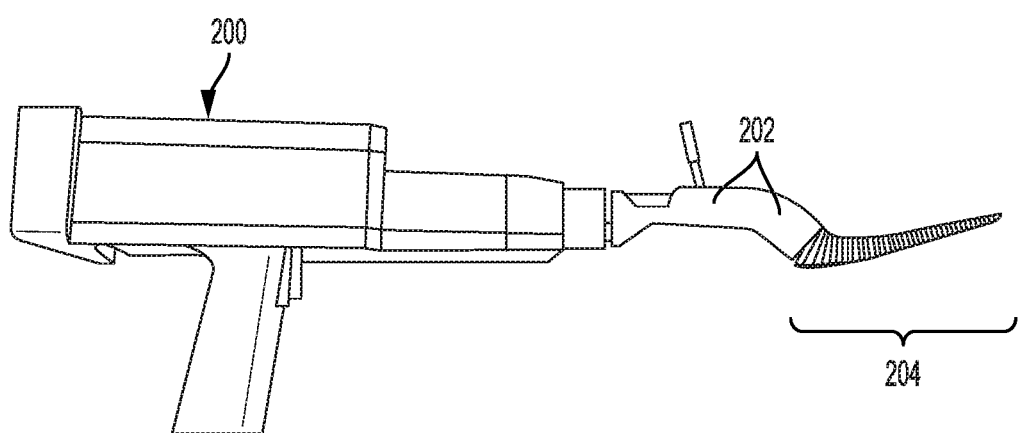
FIG. 2C shows the impactor, adapter, and surgical implement of FIG. 2B connected.

In FIGS. 2B and 2C, an impactor 200, adapter 202 and surgical implement 204 (e.g., a broach) are shown in both an unconnected state and in a connected state.

Figure 3:
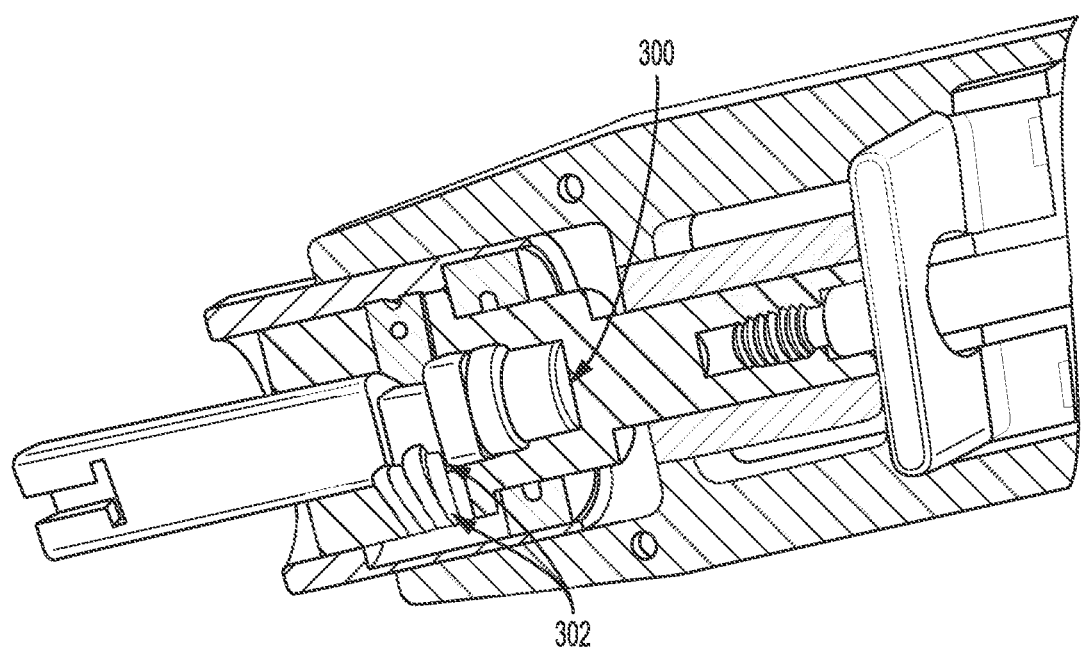
FIG. 3 shows a cross sectional view of an impactor according to an embodiment.

FIG. 3 illustrates an embodiment in which the multiple surfaces of the adapter, such as a surface for forward impacts 300 and a surface for rearward impacts 302, allow for both proximal and distal impacts on the adapter and consequently to the surgical implement. The ability to produce impacts proximally and distally is especially useful when implements become lodged in a cavity. By applying a direct reverse blow to the adapter, the lodged implement can easily be dislodged from the cavity. It was discovered by the inventor that the surface areas should be designed to withstand impact forces ranging from 1 kilonewton to 50 kilonewtons, and more particularly about 15 kilonewtons, for general durability over time as a surgical impactor. In one example, the area of contact between the impactor 200 and either the surface for forward impacts 300 or the surface for rearward impacts 302 should be between 20 mm$^2$ and 200 mm$^2$ to transfer and withstand the necessary impact forces.

Figure 5:
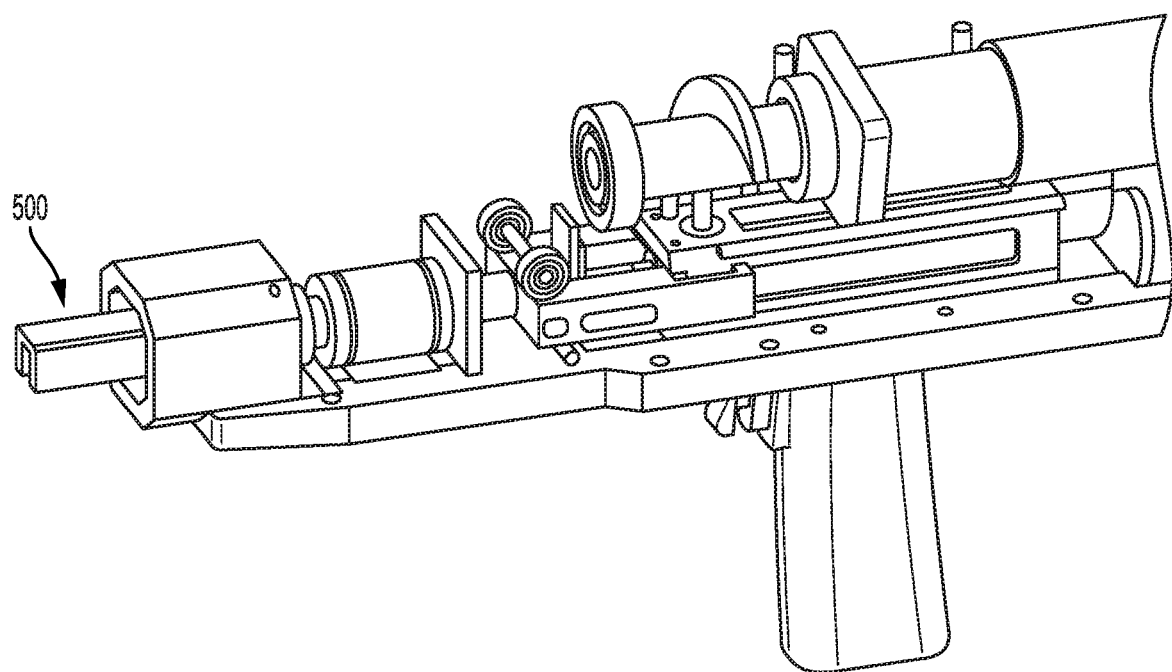
FIG. 5 shows an exemplary position for measurement of TIR for an adapter connected to the output of an orthopedic impacting tool according to one embodiment.

FIG. 5 illustrates a position on the adapter where the total indicator reading ("TIR") of the adapter can be measured. As shown in the figure, the TIR of the adapter should be measured at the tip 500 of the adapter, and in some embodiments, the adapter should be designed such that the TIR is less than 5 mm and more preferably less than 2 mm. With a small TIR, the precision of the orthopedic impactor is increased. In use, this precision translates into minimized distortion of the cavity, less energy loss laterally, improved fitting of implants, and improved surgical outcomes. By comparison, other known surgical implements have TIRs on the order of 20 mm. A TIR of 2 mm or less is a significant improvement and produces cavities with significantly more precise forms and shapes.

Figure 6A:
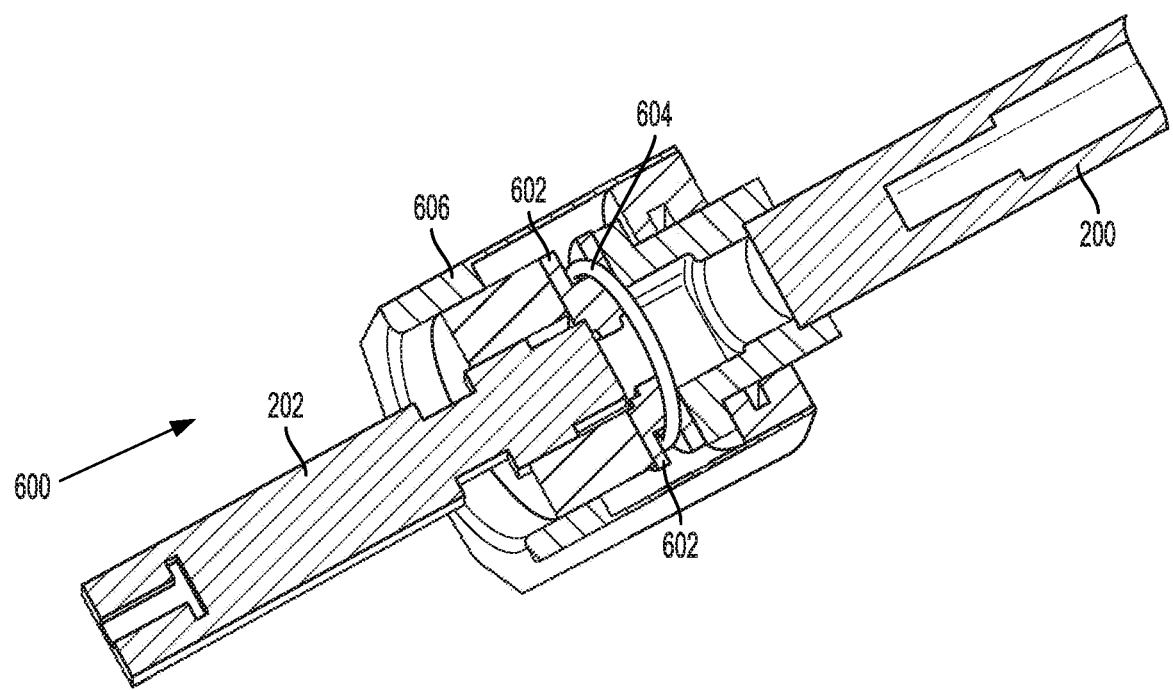
FIG. 6A shows an example adapter, with a reciprocal sleeve, on insertion of the adapter on the orthopedic impacting tool according to an embodiment.
Figure 6B:
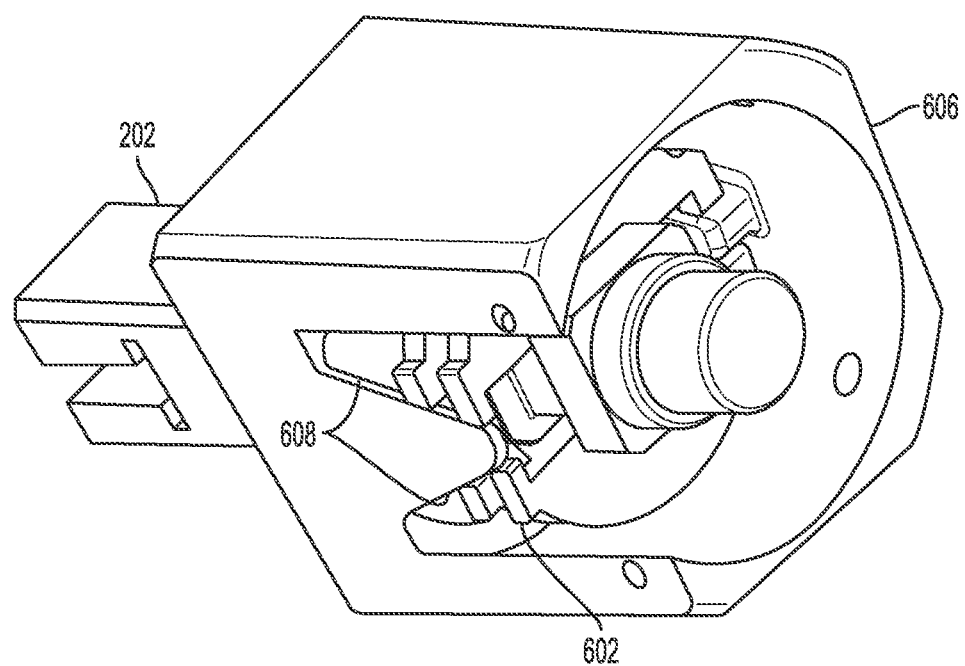
FIG. 6B shows another example adapter, with a reciprocal sleeve, on removal of the adapter from the orthopedic impacting tool according to an embodiment.

FIGS. 6A and 6B illustrate one embodiment of the insertion and removal procedures of the adapter connection to the impactor via a reciprocal sleeve.

In one embodiment, the reciprocal sleeve can include a release collar 606, snap ring 604, and retaining clips 602. As shown in FIG. 6A, the adapter 202 is inserted via a single insertion motion 600, towards the impactor, to secure the connection to the impactor 200. During that motion, retaining clips 602 within a release collar 606 are forced apart as the adapter 202 moves inward. A snap ring 604 locks, or otherwise seats and holds, in place the retaining clips 602 on the adapter 202. In one example, the snap ring 604 can be an o-ring. In other embodiments, the retaining clips 602 may be locked into place using a garter spring to exert inward radial force, maintaining position of the retaining clips 602. In further embodiments, the snap ring 604 may include an elastomer ring.

As shown in FIG. 6B, the adapter 202, in some embodiments, can be disconnected from the impactor by depressing a release collar 606. The release collar 606 includes cam surfaces 608 configured to separate the retaining clips 602 as the release collar 606 slides and gradually moves from contacting the retaining clips 602 at the narrower section of cam surfaces 608 to the wider section of cam surfaces 608. When the retaining clips 602 are separated enough to clear the adapter 202, the adapter 202 may be moved outward away from the impactor 200. In an alternative example, the reciprocal sleeve may include a pinion and rack in place of cam surfaces 608 to separate the retaining clips 602 as the adapter 202 is disconnected from the impactor.

Figure 7:
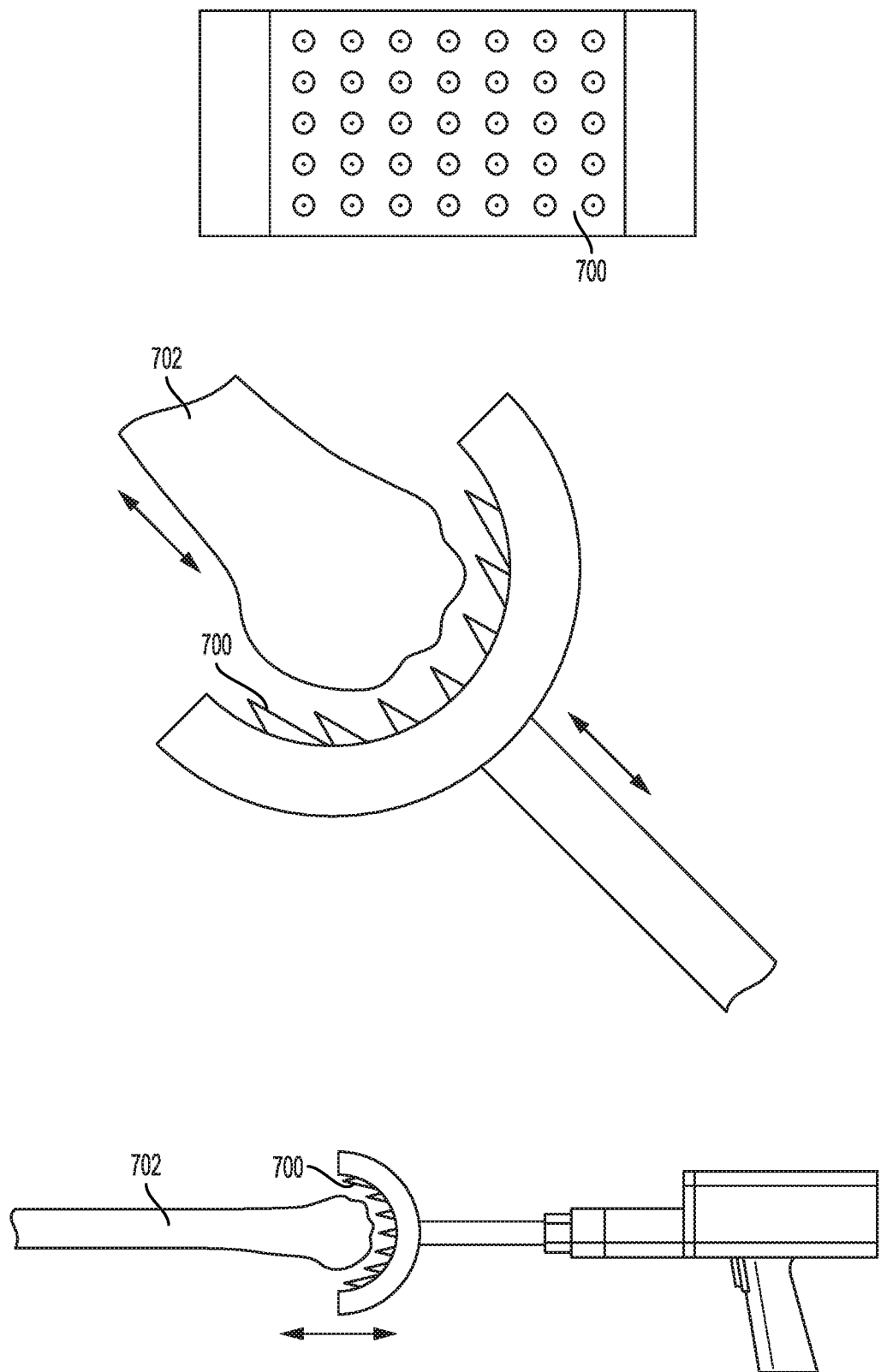
FIG. 7 shows an orthopedic implement, according to an embodiment, used to shape a bone by providing cutting teeth in at least one direction.

As shown in FIG. 7, a surgical implement for use with the adapter and an electrically driven orthopedic impactor has cutting teeth 700 for shaping a bone 702 to accept an implant. In one example, the cutting teeth 700 can be arranged on a surface of the impactor such that the teeth 700 cut linearly with an axis of the impactor. In a further embodiment, the teeth may be configured in such a fashion as to improve the fitment of a press fit implant such as a knee. In still a further embodiment, the surgical implement for use with the adapter may include features which increase the surface area available for bonding with adhesive implants.

Figure 8:
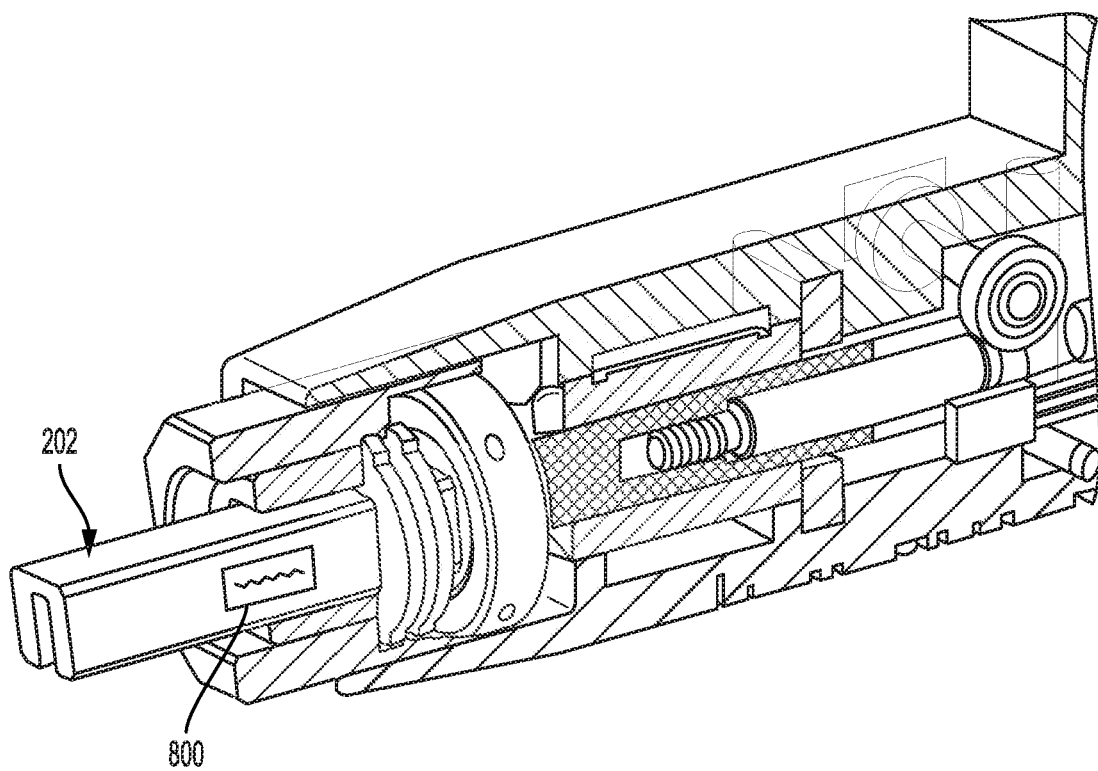
FIG. 8 shows an adapter, according to an embodiment, including a feature that communicates with the impactor or surgical implement.

FIG. 8 illustrates an example of a sensor 800 included on the adapter 202, which communicates information to the impactor and allows the surgeon to control the impactor more accurately. The information may be used, for example, by a controller such as the controller 21 of FIG. 1 to adjust the stroke, power, or frequency of impacts, for example. For instance, if the adapter is being used in seating a head ball, where continuous impacting is not desired, the adapter sensor may be configured to communicate back to the impactor a requirement for single-shot actuation rather than repeated impacts. In this situation, surgical outcomes will be improved, as the surgeon will be less likely to cause implant subsidence during head ball impaction. The adapter may detect the surgical implement and its type or configuration information, such as in the head ball placement tool example above, by communicating with the surgical implement using the same sensor or a second sensor or other communication device. For example, the sensor may communicate an identification signal or code interpreted by the controller 21 and used by the controller 21 to adjust basic settings to those appropriate to the particular surgical implement. In a particular example, an RFID sensor on the adapter may query a passive RFID tag of the surgical implement to determine a type of the surgical implement, and provide the identification signal or code derived from the passive RFID tag to the controller 21. In another example, a physical marking upon the surgical implement may be mechanically identified (e.g., "keyed" to the adapter) or electronically identified (e.g., "scanned" by a scanning sensor of the adapter) to determine a type of surgical implement connected to the adapter. The settings, in some examples, can include a frequency of impact, a force of impact, and/or a direction of impact. In some embodiments, the surgical implement is integrally formed with, and thus not detachable from, the adapter. In those embodiments, the adapter may store information relating to the surgical implement and communicate the information to the surgical impactor.

As another example, communication and control of frequency information allows the tool to precisely and consistently control the frequency of the impacting movement. By regulating the frequency of the striker, the tool may impart a greater total time-weighted percussive impact, while maintaining the same impact magnitude. This allows the surgeon better control over the cutting speed of the surgical implement. For example, the surgeon may choose cutting at a faster rate (higher frequency impacting) during the bulk of the surgical implement movement and then slow the cutting rate as the surgical implement approaches a desired depth. In fact, during testing of the tool, it was discovered that a higher frequency impacting rate, such as 3 impacts per second, preferably up to 10 impacts per second, coupled with a substantially constant energy per impact, delivering between 2 to 6 joules per second, preferably up to 40 joules per second, allowed the surgeon to better position certain surgical implements. This was seen, for example, in the seating of an acetabular cup, where an impact frequency of at least 3 impacts per second, at an energy of between 2 and 6 joules per second, resulted in far better control of the position of the acetabular cup over the prior art manual hammering technique. In a further unexpected benefit of the rapid impacting capabilities of the electric driven orthopedic impactor, the inventor discovered that the energy to perform an operation could be reduced as the movement of the surgical implement was more fluid and continuous (i.e., less of a start and stop function similar to mallet blows). This benefit of rapid impacting (e.g., at a rate greater than 3 times per second) finds its basis in engineering differences between static and dynamic friction. Dynamic friction is almost always less than static friction, and as such, a more continuous movement of a broach, implant, or other surgical implement allows for lower overall forces during the operation. In addition, it has been the inventor's experience in the operating room that the near continuous movement of the surgical implement not only lowers the total energy required but also results in a better surgical outcome. In a specific case of a reamed acetabulum, a reamer may leave valleys and peaks. By using a more continuous or higher frequency impacting described herein, the valleys and peaks are reduced and in effect ironed out. This has been clearly seen in numerous cadaver labs. Specifically, in the placement of the cup into the acetabulum, better fixation results from the more intimate contact between the surfaces.

Information communicated between the adapter, the impactor, and the surgical implement may be in the form of settings or other identification information, which are then referenced (e.g., by the controller 21) in tables or databases to determine the configuration settings as discussed in the examples above. Communication between the adapter, the surgical impactor, and the surgical implement can be performed in a variety of ways, including mechanically, magnetically, electrically, or wirelessly. For example, a short range wireless communication protocol, such as radio-frequency identification (RFID) or Bluetooth®, may be used to transfer information between the adapter, impactor, and surgical implement. In one embodiment, passive RFID technology may be used to retrieve information related to the type of surgical implement, thereby avoiding providing a power source within the surgical implement. In another example, a manual speed setting such as a speed dial may transfer a mechanical signal to the surgical impactor, thereby triggering adjustment of the impacting rate at the controller.

While certain embodiments have been described, these embodiments have been presented by way of example only, and are not intended to limit the scope of the present disclosures. Indeed, the novel methods, apparatuses and systems described herein can be embodied in a variety of other forms; furthermore, various omissions, substitutions and changes in the form of the methods, apparatuses and systems described herein can be made without departing from the spirit of the present disclosures. The accompanying claims and their equivalents are intended to cover such forms or modifications as would fall within the scope and spirit of the present disclosures.

What is claimed is:

1. An adapter configured to interface a surgical implement at a forward end of the adapter, with an electrically driven surgical impacting tool, the surgical impacting tool including an anvil and being configured to produce energy to move the anvil forward or rearward along an anvil axis, the adapter comprising:
   a forward impact surface configured to engage a corresponding forward impact surface of the surgical impacting tool;
   a rearward impact surface, distinct from, and disposed opposite, the forward impact surface, the rearward impact surface configured to engage a corresponding rearward impact surface of the surgical impacting tool; and
   a first surface, a second surface, and a third surface, the first, second, and third surfaces forming distinct and respective first, second, and third planes that are each substantially parallel to the anvil axis, wherein the first surface, the second surface, and the third surface allow for the adapter to be positioned with respect to the surgical impacting tool at distinct and respective first, second, and third rotational positions around the anvil axis;
   wherein the forward impact surface is configured to receive a forward impact force such that the forward impact force is communicated through the adapter to the surgical implement, and wherein the rearward impact surface is configured to receive a rearward impact force such that the rearward impact force is communicated through the adapter to the surgical implement.

2. The adapter of claim 1, wherein the forward impact surface and the rearward impact surface each contact the anvil with an area between 20-200 mm$^2$ during the operation of the surgical impacting tool.

3. The adapter of claim 1, further comprising a fourth surface forming a fourth plane, distinct from the first, second, and third planes, that is substantially parallel to the anvil axis and that allows for the adapter to be positioned with respect to the surgical impacting tool at a fourth rotational position about the anvil axis distinct from the first, second, and third rotational positions.

4. The adapter of claim 1, wherein a surface proximal to the surgical impacting tool is configured to allow the adapter to connect to the surgical impacting tool with a single motion along or parallel with the anvil axis.

5. The adapter of claim 1, wherein the forward impact surface or the rearward impact surface is configured to engage and disengage a release collar connected to the surgical impacting tool to connect and disconnect the adapter from the surgical impacting tool.

6. The adapter of claim 5, wherein the release collar is configured to disengage from the adapter by sliding the release collar toward the surgical impacting tool.

7. The adapter of claim 1, wherein the adapter and the surgical implement are a single component.

8. The adapter of claim 1, wherein the first surface and the second surface are orthogonally oriented relative to one another.

9. A surgical system comprising the adapter and the surgical implement of claim 1 configured to receive the forward impact force and the rearward impact force.

10. An adapter configured to interface a surgical implement at a forward end of the adapter with an electrically driven surgical impactor, the surgical impactor including an anvil and being configured to produce energy to move the anvil along an anvil axis, the adapter comprising:
  a surface oriented substantially perpendicular to the anvil axis and configured to receive an impact force in a first direction and to communicate the impact force in the first direction to the anvil in the first direction along the anvil axis; and
  a first surface, a second surface, and a third surface, the first, second, and third surfaces forming distinct and respective first, second, and third planes that are each substantially parallel to the anvil axis, wherein the first surface, the second surface, and the third surface allow for the adapter to be positioned with respect to the surgical impactor at distinct and respective first, second, and third rotational positions around the anvil axis.

11. The adapter of claim 10, wherein the surface substantially perpendicular to the anvil axis contacts the anvil with an area between 20-200 mm$^2$ during the operation of the surgical impactor.

12. The adapter of claim 10, further comprising a fourth surface forming a fourth plane, distinct from the first, second, and third planes, that is substantially parallel to the anvil axis and that allows for the adapter to be positioned with respect to the surgical impactor at a fourth rotational position about the anvil axis distinct from the first, second, and third rotational positions.

13. The adapter of claim 10, wherein a surface proximal to the surgical impactor is configured to allow the adapter to connect to the surgical impactor with a single motion along or parallel with the anvil axis.

14. The adapter of claim 10, wherein the surface substantially perpendicular to the anvil axis is configured to engage and disengage a release collar connected to the surgical impactor to connect and disconnect the adapter from the surgical impactor.

15. The adapter of claim 14, wherein the release collar is configured to disengage from the adapter by sliding the release collar along or parallel with the anvil axis.

16. The adapter of claim 10, wherein the adapter and the surgical implement are a single component.

17. The adapter of claim 10, wherein the first surface and the second surface are orthogonally oriented relative to one another.

18. A surgical system comprising the adapter and the surgical implement of claim 10 configured to receive the impact force.

* * * * *